United States Patent [19]

Leston

[11] 4,423,253
[45] Dec. 27, 1983

[54] PROCESS FOR SEPARATING T-BUTYLATED PHENOLS

[75] Inventor: Gerd Leston, Pittsburgh, Pa.

[73] Assignee: Koppers Company, Inc., Pittsburgh, Pa.

[21] Appl. No.: 372,056

[22] Filed: Apr. 26, 1982

[51] Int. Cl.$^3$ ............................................. C07C 37/68
[52] U.S. Cl. .................................... 568/756; 568/749; 568/750; 568/751; 568/784
[58] Field of Search ............... 568/750, 784, 749, 751, 568/752, 756

[56] References Cited

U.S. PATENT DOCUMENTS

| | | |
|---|---|---|
| 3,341,607 | 9/1967 | Leston ................................ 568/756 |
| 4,267,389 | 5/1981 | Leston ................................ 568/756 |
| 4,267,390 | 5/1981 | Leston ................................ 568/750 |
| 4,267,391 | 5/1981 | Leston ................................ 568/750 |
| 4,267,392 | 5/1981 | Leston ................................ 568/750 |

OTHER PUBLICATIONS

Sharpless et al., "J. Org. Chem." vol. 40 (1975), pp. 1252–1257.

*Primary Examiner*—Werren B. Lone
*Attorney, Agent, or Firm*—J. Timothy Keane; Daniel J. Long; Herbert J. Zeh, Jr.

[57] ABSTRACT

A process is disclosed for separating t-butylated phenolic compounds from other t-butylated and unbutylated phenolics by treating a mixture of the phenolics with a metal halide salt. The metal halide salt preferentially forms a complex with one of the phenolics over other related phenolics in the mixture. The preferentially-formed complex of one of the phenolics may then be isolated from the mixture and the complex decomposed to provide a product substantially enriched in, or substantially entirely composed of, one phenolic. The process is particularly suitable for resolving a mixture comprising phenol or cresol from their ortho-t-butylated derivatives, or a mixture of two isomeric t-butylated phenols or cresols or a mixture of mono- and di-t-butylated phenols or cresols.

24 Claims, No Drawings

PROCESS FOR SEPARATING T-BUTYLATED PHENOLS

BACKGROUND OF THE INVENTION

1. Field of the Invention

Preferential complexation of one organic compound in a mixture of related compounds is a known technique for resolving mixtures of closely related compounds. Of particular interest herein are methods for resolving mixtures of phenolic compounds, at least one of which is a t-butylated phenolic, by preferential complexation of one of the phenolics.

2. State of the Art

Mixtures of t-butylated phenolics are available as end-products or by-products of many commercial t-butylation reactions involving the t-butylation of phenol and cresols. The isolation and purification of individual t-butylated phenolics is very difficult by the use of conventional separation methods such as fractional distillation, which tends to cause de-t-butylation and, therefore, leads to impure phenolics.

There are chemical processes known for separating closely-related organic compounds by methods other than, or in addition to, energy-intensive physical separation techniques such as fractional distillation or fractional crystallization. These chemical processes involve a step of preferential complexation of one component of a mixture of closely-boiling compounds over other components of the mixture. For example, U.S. Pat. No. 4,267,389 to Leston, describes treating a phenolic mixture comprising para-cresol, methylated phenols and ethylated phenols, with an inorganic halide salt, such as calcium bromide to remove para-cresol from the mixture. Removal of para-cresol from the mixture involves formation of a complex between para-cresol and calcium bromide, which complex forms preferentially over complexes between calcium bromide and other components of the phenolic mixture.

Mixtures of various alcohols may be resolved by treatment with a halide salt. For example, in Sharpless et al., J. Org. Chem., Vol. 40, No. 9, p.p. 1252–1257 (1975), there is reported a study of competition between pairs of mono-hydroxy alcohols and mono-hydroxy phenols for complex formation with a halide salt. This study finds that phenols as a class form poorer complexes than alcohols of comparable melting point, probably because the phenols are weaker bases than the comparable alcohols.

There remains need, therefore, for methods for resolution of mixtures fo closely-related t-butylated phenolics by chemical complexation methods, rather than by fractional crystallization or distillation.

SUMMARY OF THE INVENTION

A mixture of two or more phenolics some or all of which are t-butylated, may be resolved into individual phenolic components by a process involving a step of forming a solid complex preferentially between a metal halide salt and one of the phenolics in the mixture containing at least one t-butylated phenolic. A metal halide salt suitable for forming the solid complex may be selected from the group consistng of calcium bromide, calcium chloride, lithium bromide, magnesium chloride and magnesium bromide. Resolution of such phenolic mixture may be accomplished by either of the following two preferred methods.

A first method involves bringing together a mixture of two or more phenolics at least one of which is a t-butylated phenolic, and a selected metal halide salt, the metal halide being selected such that a complex forms with one of the phenolics in preference to, or preferentially over, other phenolics in the mixture. This preferentially formed complex constitutes a solid material in contact with a liquid phase such as may be provided by aliphatic, alicyclic and aromatic hydrocarbons, and their chlorinated derivatives, ethers, esters and ketones. Also, any combination of such solvents may be used. Alcohols are specifically excluded as solvents inasmuch as they form complexes with the metal halide salt solvent. The solid complex may then be removed or isolated from the liquid phase and thereafter decomposed to a product comprising a predominantly greater amount of the preferentially-complexed phenolic than other phenolics, as compared to the relative amounts of phenolics present in the original mixture. The product may also contain phenolic derived from complexes which form with the selected metal halide salt, but in lesser amount than the amount of phenolic derived from the preferentially-formed complex.

A second method involves forming a mixture of two or more phenolics, at least one of which is a t-butylated phenolic, in contact with a selected metal halide salt, the metal halide salt initially present in an amount relative to one phenolic and selected such that one or more complexes form between the selected metal halide salt and one or more of the phenolics, but such that at least one of the phenolics forms no complex or forms a significantly lesser amount of complex with the selected metal halide salt than the preferentially-complexed phenolic. This phenolic which forms no complex, or which forms a complex in a significantly lesser amount than other phenolics, relative to amounts of phenolics originally present in the mixture, remains dissolved in the liquid phase. The solvent providing the liquid phase may then be removed or isolated from the preferentially-complexed phenolics which are present as solid material. Removal of the solvent provides a product containing an enriched amount of the phenolic which did not preferentially complex with the selected metal halide salt, as compared to the original mixture of phenolics.

One advantage provided by the process of the invention is good resolution or mutual separation of pairs of phenolics can be obtained from a mixture of two or more phenolics which separation would be substantially impossible to accomplish in a one-stage fractional distillation or separation because of possible de-t-butylation. A second advantage resides in this chemical-separation process requiring significantly less energy to accomplish good resolution of the phenolics than physical-separation methods such as fractional distillation or crystallization.

The chemical-separation process of the invention may also be used advantageously in conjunction with conventional physical-separation processes. For example, calcium bromide complexation may be used in an initial treatment of a phenolic mixture for separating three or more compounds. Then, a resulting mixture of compounds having boiling points further apart can be treated by distillation or crystallization of more complete resolution of the mixture.

DETAILED DESCRIPTION OF THE INVENTION

The term "phenolic" or "phenolics" as used herein includes phenol, cresols and t-butylated derivatives of phenol and cresols. The term "t-butylated derivative" as used herein designates a phenolic wherein one or more of the hydrogens on the aromatic ring is replaced by a t-butyl group. The phrases "resolving a mixture of phenolics" and "resolution of a mixture of phenolics" relate to a mechanism or a result in which the individual phenolic components of a mixture containing two or more phenolics may be separated or isolated from each other. Thus, the separation of a significant amount of one phenolic from a mixture of two phenolics constitutes a resolution of the mixture. The phrases also embrace separation of a multi-component mixture into groups of phenolics, each group containing two or more phenolics. Also included within the definition are treatments resulting in a significant increase in the amount of one or more phenolics as compared to the composition of the original mixture of phenolics, even where the original mixture contained relatively small amounts of the enriched phenolic. It is contemplated that a differentation or enrichment in the relative amounts of phenolics is a "significant enrichment" if treatment of a mixture provides an increase of at least about 20 weight percent in one or more of the phenolics as compared to the composition of the original mixture.

The phrases "preferentially-formed complex" and "predominantly-complexed phenolic" are intended as abbreviated descriptions of the complex comprising a selected metal halide salt and a dihydric phenol which forms in an amount significantly greater than an amount of any other complex of another phenolic resulting from treatment of the phenolic mixture with the selected metal halide salt. Any complex formed will preferably be comprised substantially entirely of a complex of a single type of phenolic. It is recognized, however, that other phenolics in a starting mixture may form complexes with the selected salt in secondary or lesser amounts than the primary, predominantly-formed complex. Such secondary complex formation in lesser amounts is not deleterious provided that the ratio of the predominant complex to the secondary complex in the resulting solid material is sufficiently high to provide a useful resolution of a phenolic mixture. It is contemplated that a primary/secondary or predominant/lesser ratio of the relative amounts of complexes of the treated mixture constitutes a significant and usefully-resolved mixture of phenolics.

Mixtures of phenolics susceptible to treatment with the process of the invention include mixtures of two or more phenolics, one or more of which is t-butylated. Such phenolics include phenol, o-t-butylphenol, m-t-butylphenol, p-t-butylphenol, 2,6-di-t-butylphenol, 2,4-di-t-butylphenol, 2,4,6-tri-t-butylphenol, m-cresol, 6-t-butyl-m-cresol, 4-t-butyl-m-cresol, 5-t-butyl-m-cresol, 4,6-di-t-butyl-m-cresol, p-cresol, 2-t-butyl-p-cresol, 3-t-butyl-p-cresol, 2,6-di-t-butyl-p-cresol, o-cresol, 6-t-butyl-o-cresol, 4-t-butyl-o-cresol and 4,6-di-t-butyl-o-cresol.

The family of metal halide salts which may be used in the invention are characterized in having several features in common. For example, in addition to each member of the family being an inorganic salt of a metallic chloride or bromide, these halide salts are characterized in taking on water of hydration. The hydratable nature of these metal halide salts is believed to be significant in the mechanism of complex formation with the phenolics, even though no water is involved in the complexation reaction. Of the family of metal halide salts suitable for use in the invention, calcium bromide is preferred. It is also preferred, whether calcium bromide or calcium chloride or any other of the halide salts is used, that the salt have a water content, either as hydrate or occluded, of less than about ten weight percent. Also, it is preferred that the salt have a particle size less than about 200 mesh.

Solvents which may be used in the complexation reaction include those organic compounds which dissolve the phenolic mixtures but do not preferentially react with the metal halide salt. Solvents suitable include aliphatic, alicyclic and aromatic hydrocarbons, their chlorinated derivatives, ethers, esters and ketones. Alcohols are specifically excluded since they may form complexes with the metal halide salt. Mixtures of solvents may also be used.

The process of the invention is particularly suitable for resolving mixtures of closely related phenolics, one or more of which is a t-butylated phenolic. Examples of such mixtures include the following: phenol and o-t-butylphenol; m-t-butylphenol and p-t-butylphenol; p-t-butylphenol and 2,4-di-t-butylphenol; m-cresol and 6-t-butyl-m-cresol; 4-t-butyl-m-cresol and 4,6-di-t-butyl-m-cresol; p-cresol and 2-t-butyl-p-cresol. Generally, in a mixture containing the parent unbutylated phenolic and its o-t-butylated phenolic derivative, the unbutylated phenolic is preferentially complexed with calcium bromide. Generally, in mixture containing an ortho-t-butylated phenolic and a para-t-butylated phenolic, the para-t-butylated phenolic is preferentially complexed. Generally, in a mixture containing a para-t-butylated phenolic and a o,p-di-t-butylated phenolic, the para-t-butylated phenolic is preferentially complexed with calcium bromide.

Generally, the metal halide salt is added to the mixture of phenolics dissolved in, or in contact with, a solvent. For calcium bromide, for example the salt is preferably added in amount in a range from about 0.1 mole to about 4 moles to one mole of the phenolic to be preferentially complexed. Usually, the complexation reaction takes place in the presence of a catalyst such as a lower aliphatic alcohol. A typical cataytic amount of the alcohol would be approximately five mole percent of the alcohol based on the total phenolic content.

After the aforementioned components are brought together as a mixture, usually in the form of a slurry, the mixture is agitated for a period of time sufficient for the phenolic-metal halide salt complex to form. A typical mixing time is in a range from about one hour to about 24 hours. Mixing is typically conducted at room temperature and at atmospheric pressure, although the complexation reaction may be conducted at practically any temperature in a range from about 0° C. to about 150° C. Super atmospheric pressure may be used to avoid escape of reactants and solvents. Also, care must be taken to exclude ambient moisture from the reaction mixture.

After the mixing period, the mixture contains a fluffy, white or gray solid material component in contact with a liquid component. The solid material may be separated from the liquid component by any conventional separation techniques such as by decanting, by centrifugation, or by filtration. If filtration is used to separate the solid material from the liquid, the filtration may be conducted with the aid of pressure gradient applied across the filter medium. The separated solid material may be washed with small portions of solvent, and the washings thereafter may be combined with the filtrate. After the washing step, the separated solid material may be optionally dried, usually by means of low heat or in a desiccator under reduced pressure. The drying step is carried out until the solid material reaches a constant weight.

The solid material, which contains the phenolic-metal halide salt complex, is then decomposed to provide the desired phenolic. Decomposition may be accomplished by hydrolysis of the complex in water, by heating of the complex at a temperature usually in a range of from about 150° C. to about 350° C., or by treatment with an alcohol, such as a lower boiling aliphatic alcohol. Preferred decomposition methods include water hydrolysis and heat treatment of the complex. In decomposition of the complex by water hydrolysis, the phenolic may be recovered by treating the water with an organic solvent, typically ether. In decomposition of the complex with heat, the phenolic may be separated by filtration, centrifugation or distillation from the metal halide salt residue. In either of these decomposition methods, the metal halide salt may be recovered and recycled for treatment of another mixture of phenolics, or for subsequent treatment of the separated phenolics in the event of incomplete separation of the mixture of phenolics.

It is an important feature of the invention that the liquid portion of the mixture treated with the metal halide salt contains the phenolic which less predominantly forms a complex with the metal halide salt or which forms substantially no complex with the metal halide salt. Thus the liquid portion of the treated mixture will be enriched in this phenolic and depleted in the phenolic which predominantly complexes with the metal halide salt. This phenolic may be recovered from this liquid portion by conventional distillation or fractionation techniques.

In order to demonstrate the invention a series of individual t-butylated phenolics were treated with calcium bromide to show the formation of a t-butylated phenolic-$CaBr_2$ complex, as described in Examples I and II.

EXAMPLE I

A reaction vessel equipped with stirring means was charged with 15.0 g p-t-butylphenol (100 mmole), 0.2 ml absolute ethanol and 100 ml toluene as a solvent for the organic components. To the reaction vessel was added 5.0 g powdered anhydrous calcium bromide (25 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. A complexation reaction was run by stirring this mixture for about 18 hours at room temperature, after which time 125 ml toluene was added. Thereafter, the mixture was stirred about 5 minutes. The mixture was observed to contain a large amount of fluffy, white solid material suspended in the liquid solution. The mixture was filtered under suction, in a manner to minimize exposure of the mixture to ambient moisture, so as to separate the fluffy solid material from the liquid component. The separated solid material was washed with small portions of toluene and the hexane washings were combined with the filtrate. The washed solid material was dried in a desiccator under a pressure of 1 mm Hg absolute for a period of time until a substantially constant weight was recorded of 7.5 g. Inasmuch as the dried solid material weighed 7.5 g, it was determined that 2.5 g p-t-butylphenol complexed with the calcium bromide so that the molar ratio of p-t-butylphenol:calcium bromide in the complex was 0.6:1.0.

EXAMPLE II

A complexation reaction was run generally as described in Example I with a mixture of 15.0 g 2-t-butylphenol (100 mmole), 0.1 ml absolute ethanol and 5.0 g powdered anhydrous calcium bromide (25 mmole). After the mixture was stirred for a total of 18 hours it was diluted with hexane. A washed-and-dried solid material was obtained in an amount of 7.29 g. The filtrate was concentrated on a steam bath to a constant weight of 12.75 g. Inasmuch as 2.3 g o-t-butylphenol apparently complexed with 5.0 g $CaBr_2$, it was determined that the 2-t-butylphenol/$CaBr_2$ molar ratio was 0.61:1.0.

As shown in Examples III to VIII, various synthetic mixtures of phenolics, containing one or more t-butylated phenolics, were prepared for treatment with calcium bromide to show the preferential complexation of one phenolic over another phenolic, so as to allow separation of two or more phenolics. In the working examples which follow, the extracted-and-decomposed complexes of the separated solid material and the liquid portions were subjected to GC or IR analysis to determine the relative amounts of the phenolics in the solid material and in the liquid filtrate.

EXAMPLE III

A reaction vessel equipped with stirring means was charged with 7.5 g o-t-butylphenol (50 mmole) and 7.5 g p-t-butylphenol (50 mmole) along with about 0.2 ml absolute ethanol and 50 ml toluene as a solvent for the phenolics to form a solution. To the reaction vessel, there was added 10.0 g finely-ground anhydrous $CaBr_2$ (50 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. The mixture was stirred for about 16 more hours at room temperature after which time there was observed a large amount of a fluffy, white solid material suspended in the liquid solution. Then the mixture was filtered under suction, in a manner to minimize exposure of the mixture to ambient moisture, to separate the fluffy solid material from the liquid component. The separated solid was washed twice with 10 ml portions of toluene, the washings then combined with the filtrate. The washed solid was dried in a desiccator under a pressure of 1 mm Hg absolute for two hours at room temperature. The dried solid amounted to 12.76 g, a portion of which was hydrolyzed in water to form a hydrolyzate, which hydrolyzate was extracted from the water by five sequential treatments of the water containing the hydrolyzate with ether. GC analysis of the ether extract derived from the precipitate showed that the solid material contained 83.8% p-t-butylphenol and 16.2% o-t-butylphenol. Analysis of the filtrate showed 81.5% o-t-butylphenol and 18.5% p-t-butylphenol.

EXAMPLE IV

A complexation reaction was run as generally described in Example III with a starting mixture of 5.4 g p-cresol (50 mmole), 5.4 g 2-t-butyl-p-cresol, 0.2 ml absolute ethanol, 100 ml benzene and 10.0 g powered anhydrous calcium bromide. After the mixture was stirred for about 16 hours at room temperature, a washed-and-dried solid material was obtained in an amount of 12.23 g. Hydrolysis treatment and GC analysis of the solid material showed 99.8% p-cresol while the combined filtrate and washings contained 30.1% p-cresol and 69.6% 2-t-butyl-p-cresol.

EXAMPLE V

A complexation reaction was run as generally described in Example III with a starting mixture of 7.7 g 4-t-butyl-m-cresol (50 mmole), 7.7 g 6-t-butyl-m-cresol (50 mmole), 0.1 ml absolute ethanol, 100 ml benzene and 10.0 g powdered anhydrous calcium bromide (50 mmole). After the mixture was stirred for 18 total hours at room temperature, 10.58 g solid material was obtained utilizing the described isolation steps. GC analyses of the hydrolyzed and extracted solid showed 87.1% 4-t-butyl-m-cresol and 12.9% 6-t-butyl-m-cresol. The combined filtrate and washings showed 44.2% 4-isomer and 55.8% 6-isomer by GC.

EXAMPLE VI

A complexation reaction was run as generally described in Example III with a starting mixture of 5.4 g 6-t-butyl-m-cresol, 5.4 g m-cresol (50 mmole), 0.2 ml absolute ethanol, 100 ml benzene and 10.00 g powdered anhydrous calcium bromide (50 mmole). After 5 hours of mixing, 35 ml hexane was added. After the mixture was stirred for about 18 hours more at room temperature, a washed-and-dried solid material was obtained in an amount of 10.29 g. Results of GC analysis of the hydrolyzed solid showed 71.1% m-cresol and 28.9% 6-t-butyl-m-cresol, while the filtrate contained 47.2% m-cresol and 52.8% 6-t-butyl-m-cresol.

EXAMPLE VII

A complexation reaction was run as generally described in Example III with a starting mixture of 4.7 g phenol (50 mmole), 4.7 g impure o-t-butylphenol, 0.2 ml absolute ethanol, 100 ml benzene and 10.0 g powdered anhydrous calcium bromide (50 mmole). After the mixture was stirred for about 17 hours at room temperature, a washed-and-dried solid material was obtained in an amount of 13.28 g. Results of the GC analyses of the extracted hydrolyzate from the solid showed 99.0% phenol and 1.0% 2-t-butylphenol, while the combined filtrate and washings contained 43.6% phenol, 38.0% 2-t-butylphenol, 10.4% of an unknown impurity and 8.0% of a second unknown impurity.

EXAMPLE VIII

A complexation reaction was run as generally described in Example III with a starting mixture of 7.5 g 4-t-butylphenol (50 mmoles), 7.5 g of 2,4-di-t-butylphenol, 0.2 ml absolute ethanol, 100 ml benzene and 10.0 g powdered anhydrous calcium bromide (50 mmoles). After the mixture was stirred for about 18 hours at room temperature, 10.26 g of solid material was obtained utilizing the described isolation steps. Treatment and GC analysis of the solid material showed 97.1% 4-t-butylphenol and 2.8% 2,4-di-t-butylphenol. The combined filtrate and washings showed 50.7% p-t-butylphenol and 49.3% 2,4-di-t-butylphenol.

Although specific examples of the instant invention have been set forth hereinabove, it is not intended that the invention be limited solely thereto, but is to include all the variations and modifications falling within the scope of the appended claims.

What is claimed is:

1. A process for resolving a mixture of two or more phenolics at least one of which is a t-butylated phenolic, comprising the steps of:
    treating a mixture of two or more closely-boiling phenolics at least one of which is a t-butylated phenolic, said mixture having a temperature in a range from about 0° C. to about 150° C., with a metal halide salt selected from the group consisting of calcium bromide, calcium chloride, lithium bromide, magnesium chloride and magnesium bromide so as to form preferentially a complex comprised of the selected metal halide salt and one of the phenolics,
    whereby the preferentially-formed metal halide salt-phenolic complex may be isolated and thereafter decomposed to a product comprising a predominantly greater amount of one phenolic over other phenolics present, as compared to the relative amounts of phenolics present in the original mixture of phenolics.

2. The process of claim 1 wherein the phenolics of the mixture may be selected from phenol, ortho-cresol, meta-cresol, para-cresol, and t-butylated derivatives thereof.

3. The process of claim 1 wherein one of the phenolics in the mixture is an unbutylated phenol and another phenolic is an ortho-t-butylated derivative of said unbutylated phenolic.

4. The process of claim 1 wherein the mixture contains two mono-t-butylated phenolics having the t-butyl groups in isomeric positions relative to each other.

5. The process of claim 1 wherein the mixture contains two t-butylated phenolics, the first t-butylated phenolic being a para-t-butylated phenol and the second t-butylated phenolic being an ortho-para-di-t-butylated derivative of said first t-butylated phenolic.

6. The process of claim 1 wherein said selected metal halide salt calcium bromide.

7. A process for resolving a mixture of two or more phenolics at least one of which is a t-butylated phenolic, comprising the step of:
    forming a mixture of two or more phenolics in a liquid phase, at least one of which phenolics is a t-butylated phenolic, and a metal halide salt selected from the group consisting of calcium bromide, calcium chloride, lithium bromide, magnesium chloride and magnesium bromide, said mixture having a temperature in a range from about 0° C. to about 150° C., in relative amounts sufficient to form a complex between the selected metal halide salt and a first phenolics, which complex is insoluble in the solution, but such that at least one other of the phenolics either forms no complex with the selected metal halide or forms a complex in a relative amount which is significantly less than the amount of the complex formed with the first phenolic, said other phenolic remaining in the liquid phase,
    whereby phenolic product may be recovered from the liquid phase, the product comprising a predominantly greater amount of said other phenolic than was present in the original liquid phase.

8. The process of claim 7 wherein said first phenolic is an unbutylated phenolic with forms a complex with calcium bromide and wherein said other phenolic is an ortho-t-butylated derivative of said first phenolic which remains in the liquid phase in a predominantly greater amount was present.

9. The process of claim 7 wherein said first phenolic is a para-t-butylated phenol which forms a complex with calcium bromide and wherein said other is a di-t-butylated or a mono-t-butylated phenolic other than said para-t-butylated phenolic which remains in the liquid phase in a predominantly greater amount than was present in the original lquid phase.

10. A process for resolving a phenolic mixture containing meta-cresol and 6-t-butyl-m-cresol, the process comprising the steps of:
   (a) bringing together for from about one hour to about 24 hours calcium bromide and a mixture of phenolics, said mixture having a temperature in a range from about 0° to about 150° C., in amounts sufficient to form an insoluble solid material in contact with a liquid, the phenolic contained in the solid material being predominantly or substantially entirely meta-cresol present as a calcium bromide-meta-cresol complex, the phenol contained in the liquid being predominantly or substantially entirely 6-t-butyl-m-cresol; and
   (b) separating the insoluble solid material from the liquid and thereafter treating the material to decompose the complex, whereby a phenolic product is obtained comprising predominantly or substantially entirely meta-cresol.

11. The process of claim 10 wherein the molar ratio of meta-cresol:calcium bromide in the starting mixture is in a range from about 0.2:1.0 to about 5:0:1.1.

12. A process for resolving a phenolic mixture containing p-t-butylphenol and 2,4-di-t-butylphenol, the process comprising the steps of:
   (a) bringing together for from about one hour to about 24 hours calcium bromide, and a mixture of the phenolics, said mixture having a temperature in a range from about 0° C. to about 150° C., in amounts sufficient to form an insoluble solid material in contact with a liquid, the phenolic contained in the solid material being predominantly p-t-butylphenol present as a calcium bromide-p-t-butylphenol complex, the phenolic contained in the liquid being predominantly or 2,4-di-t-butylphenol; and
   (b) separating the insoluble solid material from the liquid and thereafter treating the material to decompose the complex, whereby a phenolic product is obtained comprising predominantly p-t-butylphenol.

13. The process of claim 12 further comprising the step of treating the liquid separated from the insoluble solid material to isolate phenolic which comprises predominantly 2,4-di-t-butylphenol.

14. The process of claim 12 wherein the molar ratio of p-t-butylphenol:calcium bromide in the starting mixture is in a range from about 0.2:1.0 to about 5.0:1.0.

15. A process for resolving a phenolic mixture containing phenol and o-t-butylphenol, the process comprising the steps of:
   (a) bringing together for from about one hour to about 24 hours calcium bromide, and a mixture of the phenolics, said mixture having a temperature in a range from about 0° C. to about 150° C., in amounts sufficient to form an insoluble solid material in contact with a liquid, the phenolic contained in the solid material being predominantly or substantially entirely phenol present as a calcium bromide-phenol complex, the phenolic contained in the liquid being predominantly or substantially entirely o-t-butylphenol; and
   (b) separating the insoluble solid material from the liquid and thereafter treating the material to decompose the complex, whereby a phenolic product is obtained comprising predominantly or substantially entirely phenol.

16. The process of claim 15 wherein the molar ratio of phenol:calcium bromide in the starting mixture is in a range from about 0.2:1.0 to about 5.0:1.0.

17. A process for resolving a phenolic mixture containing o-t-butylphenol and p-t-butylphenol, the process comprising the steps of:
   (a) bringing together for from about one hour to about 24 hours calcium bromide and a mixture of the phenolics, said mixture having a temperature in a range from about 0° C. to about 150° C., in amounts sufficient to form an insoluble solid material in contact with a liquid, the phenolic contained in the solid material being predominantly p-t-butylphenol present as a calcium bromide-p-t-butylphenol complex, the phenolic contained in the liquid being predominantly p-t-butylphenol; and
   (b) separating the insoluble solid material from the liquid and thereafter treating the material to decompose the complex whereby a phenolic product is obtained comprising predominantly p-t-butylphenol.

18. The process of claim 17 for further comprising the step of treating the liquid separated from insoluble solid material to isolate phenolic which comprises predominantly o-t-butylphenol.

19. The process of claim 17 wherein the molar ratio of p-t-butylphenol:calcium bromide in the starting mixture is in a range from about 0.2:1.0 to about 5.0:1.0.

20. A process for resolving a phenolic mixture containing 4-t-butyl-m-cresol and 6-t-butyl-m-cresol, the process comprising the steps of:
   (a) bringing together for from about one hour to about 24 hours calcium bromide and a mixture of phenolics, said mixture having a temperature in a range from about 0° C. to about 150° C., in amounts sufficient to form an insoluble solid material in contact with a liquid, the phenolic contained in the solid material being substantially entirely 4-t-butyl-m-cresol present as a calcium bromide-4-t-butyl-m-cresol complex, the phenol contained in the liquid being depleted of 4-t-butyl-m-cresol; and
   (b) separating the insoluble solid material from the liquid and thereafter treating the material to decompose the complex whereby a phenolic product is obtained comprising 4-t-butyl-m-cresol.

21. The process of claim 20 wherein the molar ratio of 4-t-butyl-m-cresol:calcium bromide in the starting mixture is in a range from about 0.2:1.0 to about 5.0:1.0.

22. A process of resolving a phenolic mixture containing p-cresol and 2-t-butyl-p-cresol, the process comprising the steps of:
   (a) bringing together for from about one hour to about 24 hours calcium bromide and a mixture of the phenolics, said mixture having a temperature in a range from about 0° C. to about 150° C., in amounts sufficient to form an insoluble solid material in contact with a liquid, the phenolic contained in the solid material being predominantly p-cresol present as a calcium bromide-p-cresol complex, the phenol contained in the liquid being predominantly 2-t-butyl-p-cresol; and (b) separating the insoluble solid material from the liquid and thereafter treating the material to decompose the complex, whereby a phenolic product is obtained comprising predominantly p-cresol.

23. The process of claim 22 further comprising the step of treating the liquid separated from the insoluble solid material to isolate phenolic which comprises predominantly 2-t-butyl-p-cresol.

24. The process of claim 22 wherein the molar ratio of paracresol:calcium bromide in the starting mixture is in a range from about 0.2:1.0 to about 5.0:1.0.

* * * * *